(12) United States Patent
Chen

(10) Patent No.: US 7,582,119 B2
(45) Date of Patent: Sep. 1, 2009

(54) PROSTHETIC KNEE JOINT

(76) Inventor: Sen-Jung Chen, No. 236, Sec. 3, Ho-Ping W. Rd., Taipei City (TW)

(*) Notice: Subject to any disclaimer, the term of this patent is extended or adjusted under 35 U.S.C. 154(b) by 464 days.

(21) Appl. No.: 11/523,620

(22) Filed: Sep. 20, 2006

(65) Prior Publication Data
US 2008/0071388 A1    Mar. 20, 2008

(51) Int. Cl.
*A61F 2/74* (2006.01)
*A61F 2/68* (2006.01)
*A61F 2/64* (2006.01)

(52) U.S. Cl. .............................. 623/39; 623/43; 623/44

(58) Field of Classification Search ................... 623/44, 623/43, 46
See application file for complete search history.

(56) References Cited

U.S. PATENT DOCUMENTS 2,208,275 A * 7/1940 Conner et al. ................. 623/46
2,395,120 A * 2/1946 Hinkle ........................ 623/44
2,863,274 A * 12/1958 Kelsey ........................ 56/10.1
4,090,264 A * 5/1978 Thompson ................... 623/44
4,911,709 A * 3/1990 Marlow et al. ............... 623/39
7,087,091 B1 * 8/2006 Chen ........................... 623/44

* cited by examiner

*Primary Examiner*—Thomas J Sweet
*Assistant Examiner*—Jacqueline Woznicki
(74) *Attorney, Agent, or Firm*—Ladas & Parry LLP (57) ABSTRACT

A prosthetic knee joint includes a knee seat having a slant screw hole, a movable member disposed pivotally in a bottom portion of the knee seat and having a lower mounting portion and an upper pushing portion, two shafts disposed respectively within shaft holes in the lower mounting portion, two C-shaped elastic sleeves sleeved respectively on the shafts and abutting against the upper pushing portion, a linkage connected to the shafts, a weight-buffering device having a rubber cushion disposed directly under the slant screw hole, a buffer adjustment device having a buffer cushion that protrudes outwardly of the movable member to abut against a projection of the knee seat and that is removable from the projection, and a restoring device operable so as to move a free end of the upper pushing portion relative to the lower mounting portion.

3 Claims, 9 Drawing Sheets

PROSTHETIC KNEE JOINT

BACKGROUND OF THE INVENTION

1. Field of the Invention

The invention relates to a prosthetic knee joint, more particularly to a prosthetic knee joint that can effectively prevent a prosthesis wearer from falling backward when walking down an inclined surface.

2. Description of the Related Art

Figure 1:
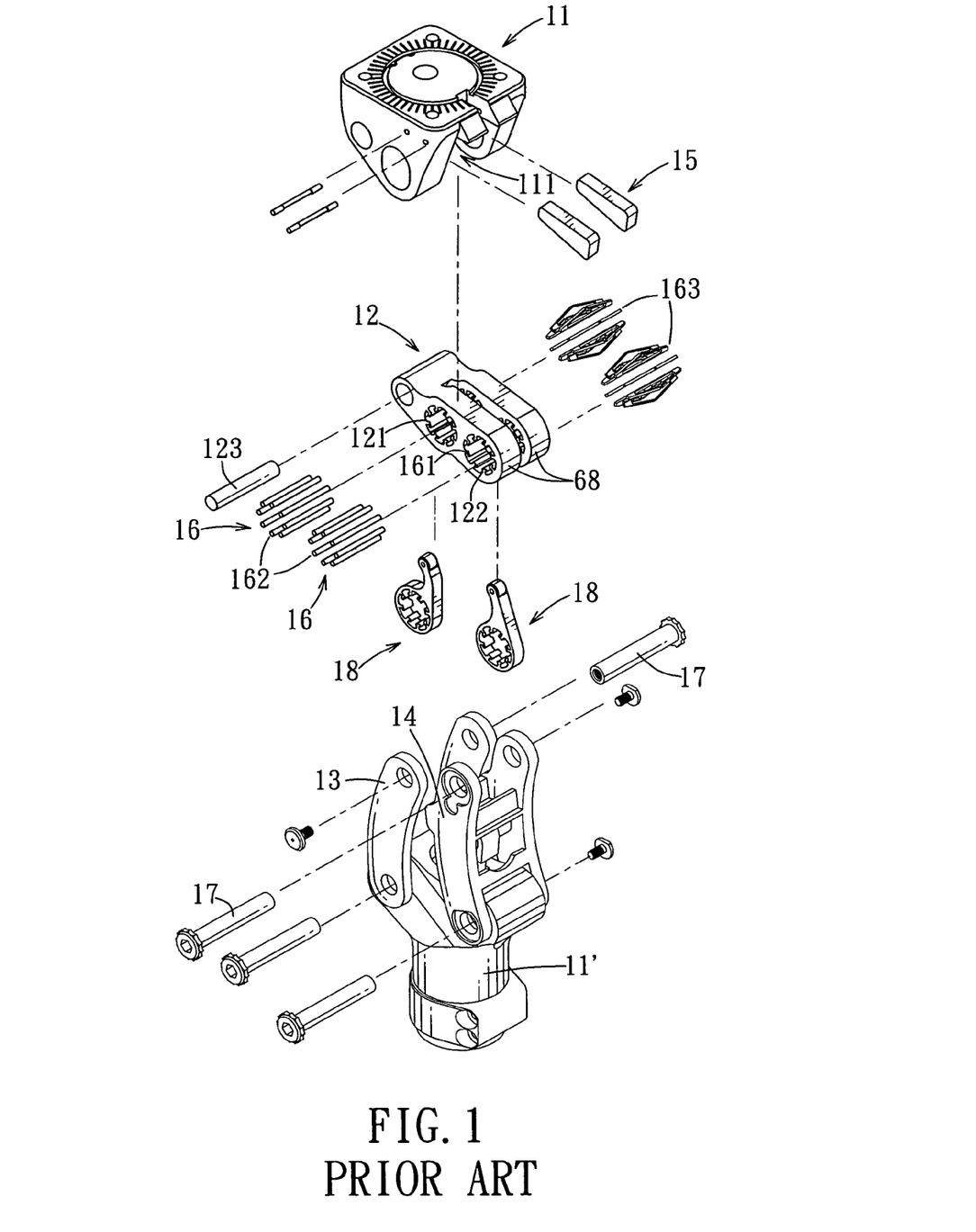
FIG. 1 is a partly exploded perspective view of a conventional artificial knee joint disclosed in Taiwanese Patent No. M284363.

Referring to FIG. 1, a conventional artificial knee joint having a minimum knee angle, as disclosed in Taiwanese Patent No. M284363, includes a knee seat 11 attached to a residual thigh (not shown) and having a bottom end formed with a mounting recess 111, a support frame 11' attached to a prosthetic lower leg (not shown), a driving member 12 disposed pivotally in the mounting recess 111 by means of a pivot pin 123, two links 13, 14 having lower ends connected pivotally to the support frame 11', a cushion device consisting of two rubber blocks 15 disposed in the mounting recess 111 and between the knee seat 11 and the driving member 12, two bearing members in the form of unidirectional bearings 16, two pivot pins 17 extending respectively through upper ends of the links 13, 14 and journalled respectively within two mounting holes 121, 122 in the driving member 12 by the bearing members, and two pin-locking members 18 sleeved respectively and rotatably on the pivot pins 17. Each unidirectional bearing 16 includes a plurality of angularly equidistant L-shaped projections 161, a plurality of rollers 162, and a plurality of unitary resilient members 163.

Although the aforementioned artificial knee joint can achieve its intended purpose, there is a need to provide an artificial knee joint with a more simple structure and that operates to help prevent a wearer from falling when walking down an inclined surface.

SUMMARY OF THE INVENTION

Therefore, the object of the present invention is to provide a prosthetic knee joint that has a simple structure and that has a movable member which can effectively prevent a prosthesis wearer from falling when walking down a sloped surface.

According to this invention, a prosthetic knee joint is adapted to be connected between a prosthetic or residual thigh and a prosthetic lower leg. The prosthetic knee joint comprises a knee seat, a movable member, a linkage, a weight-buffering device, a buffer adjustment device, and a restoring device. The knee seat has a top portion adapted to be connected with the prosthetic or residual thigh, a bottom portion connected fixedly to the top portion and defining a receiving groove, a projection projecting downwardly from the top portion into the receiving groove, a slant screw hole formed in a rear end of the top portion, and a threaded hole transverse to and in spatial communication with the slant screw hole. The movable member is disposed pivotally in the receiving groove, and includes a lower mounting portion connected pivotally to the bottom portion of the knee seat, an upper pushing portion having a connecting end connected integrally to the lower mounting portion and a front free end movable upwardly and downwardly relative to the lower mounting portion, and a slit defined between the lower mounting portion and the upper pushing portion. The lower mounting portion is formed with two spaced-apart shaft holes extending in a left-to-right direction and proximate to the connecting end of the upper pushing portion, and a first aperture and a threaded slot that are proximate to the free end of the upper pushing portion and that are in spatial communication with the slit. Each of the shaft holes has a top part partially communicated with the slit. The upper pushing portion is formed with a second aperture having an upper receiving section in spatial communication with the receiving groove, and a lower threaded section in spatial communication with the first aperture and the slit and spaced apart from the first aperture at a predetermined distance. The upper pushing portion is further formed with a receiving slot in spatial communication with the threaded slot and the slit. The movable member further includes two shafts disposed respectively within the shaft holes, and two C-shaped elastic sleeves disposed respectively within the shaft holes, sleeved respectively on the shafts, and abutting against the upper pushing portion. The linkage is adapted to be connected to the prosthetic lower leg, and has front and rear link units connected fixedly and respectively to the shafts. The upper pushing portion is movable toward the lower mounting portion so as to cooperate with the lower mounting portion to clamp the shafts within the sleeves, respectively, to thereby prevent relative movement of the front and rear link units, and is movable away from the lower mounting portion so as to allow for relative movement of the front and rear link units. The weight-buffering device includes a rubber cushion disposed between the top portion of the knee seat and the upper pushing portion of the movable member and disposed directly under the screw hole, an externally threaded control member engaging the slant screw hole and having a bottom end abutting against the rubber cushion, and a lock bolt engaging the threaded hole and abutting against the control member for locking the control member releasably within the slant screw hole. The buffer adjustment device includes a buffer cushion disposed within the upper receiving section of the second aperture and protruding partially out of the movable member so as to abut against the projection, and an adjustment bolt having a lower section extending into the first aperture, and an upper section engaging the lower threaded section of the second aperture and abutting against a bottom end of the buffer cushion. The adjustment bolt is adjustable so as to allow the buffer cushion to move away from the projection. The restoring device includes an elastic body disposed in the receiving slot, and a screw engaging the threaded slot and having a top end abutting against a bottom end of the elastic body. The screw is operable so as to move the free end of the upper pushing portion relative to the lower mounting portion.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Before the present invention is described in greater detail, it should be noted that like elements are denoted by the same reference numerals throughout the disclosure.

Referring to FIGS. 2 to 7, the first preferred embodiment of a prosthetic knee joint according to the present invention is adapted to be connected between a prosthetic or residual thigh (not shown) and a prosthetic lower leg (not shown) of a prosthesis wearer, and is shown to comprise a knee seat 5, a movable member 6, a weight-buffering device 7, a buffer adjustment device 8, and a restoring device 9.

Figure 2:
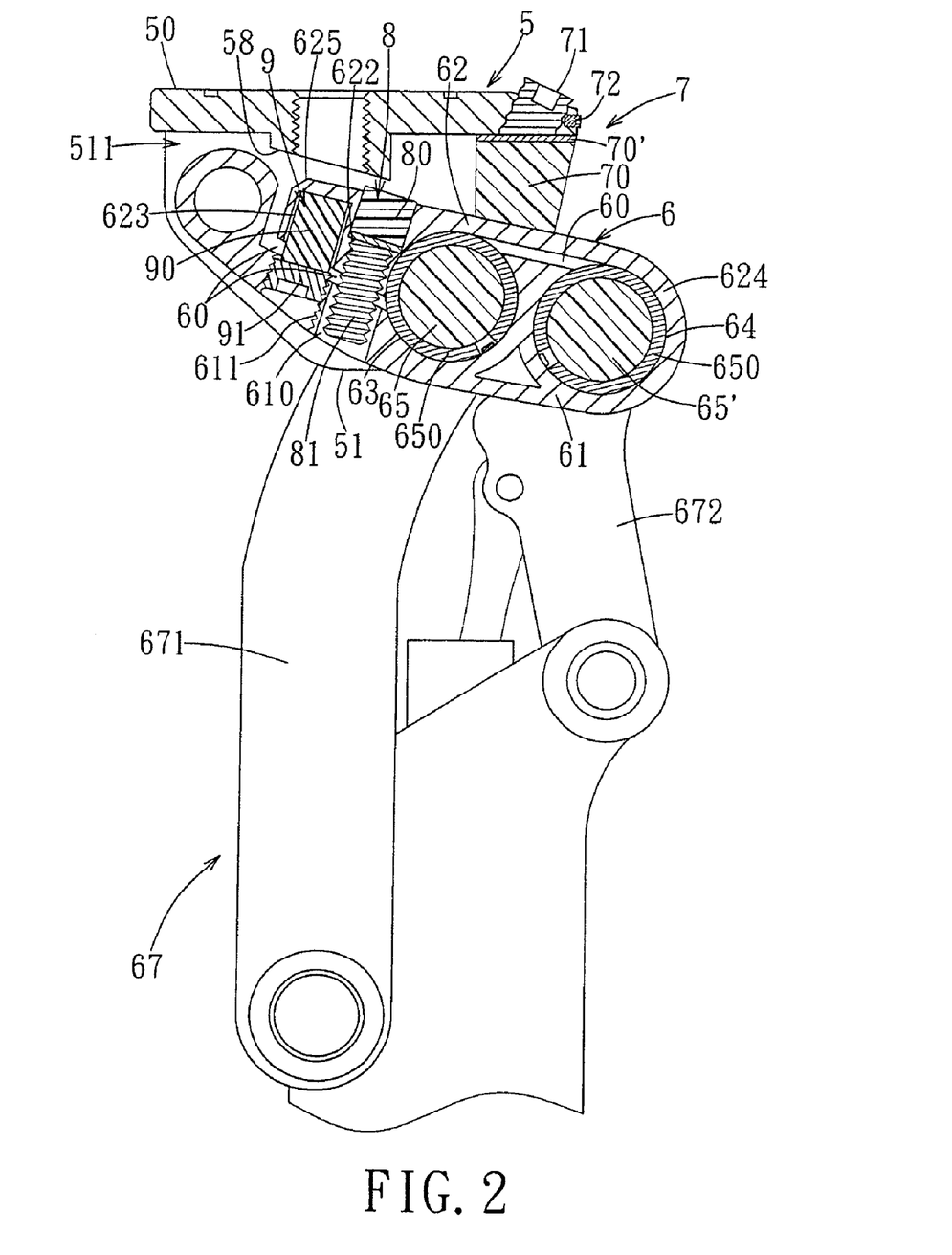
FIG. 2 is a partly sectional view of the first preferred embodiment of a prosthetic knee joint according to the present invention.
Figure 4:
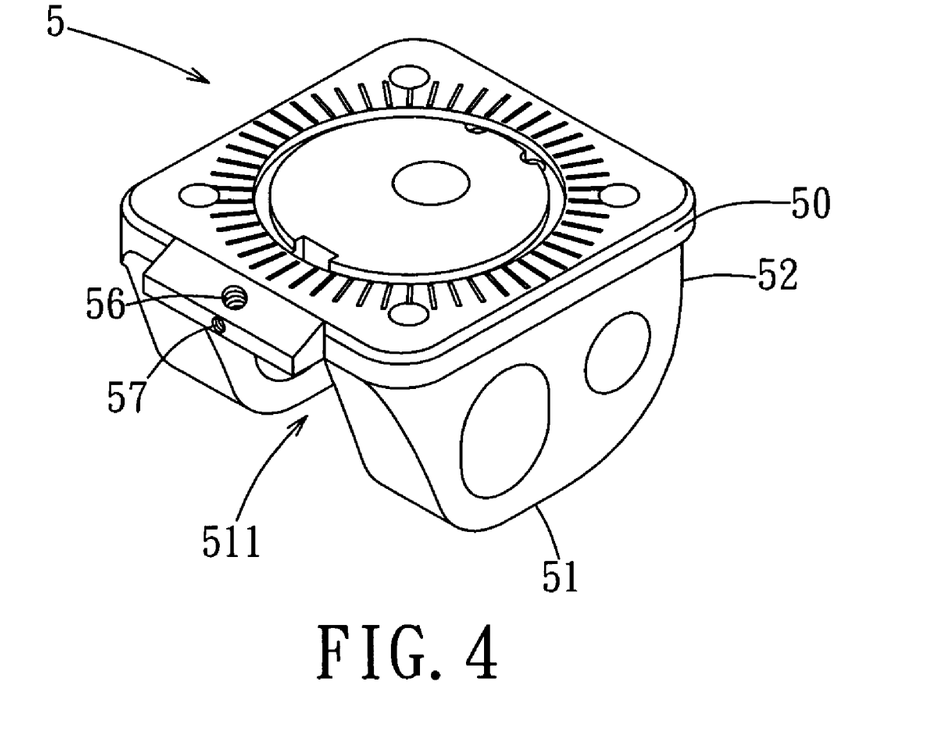
FIG. 4 is a perspective view of a knee seat of the first preferred embodiment.

The knee seat 5 has a top portion 50 adapted to be connected to the prosthetic or residual thigh of the prosthesis wearer, a bottom portion 51 connected fixedly to the top portion 50 and defining a receiving groove 511, a pivot hole 54 formed through the knee seat 5 and proximate to a front side 52 thereof, and a shaft hole 55 formed through the knee seat 5 and proximate to a rear side 53 thereof. Each of the pivot hole 54 and the shaft hole 55 has a middle hole section in spatial communication with the receiving groove 511. The knee seat 5 further has a slant screw hole 56 formed in a rear end of the top portion 50, and a threaded hole 57 transverse to and in spatial communication with the slant screw hole 56. A projection 58 projects downwardly from the top portion 50 into the receiving groove 511.

The movable member 6 is disposed pivotally in the receiving groove 511, and has a slit 60 extending in a front-to-rear direction so as to divide the movable member 6 into a lower mounting portion 61 and an upper pushing portion 62. The lower mounting portion 61 is connected pivotally to the bottom portion 51 of the knee seat 5. The upper pushing portion 62 has a connecting end 624 connected integrally to the lower mounting portion 61, and a front free end 625 movable upwardly and downwardly relative to the lower mounting portion 61. The lower mounting portion 61 is formed with two spaced-apart shaft holes 63, 64 extending in a left-to-right direction and proximate to the connecting end 624 of the upper pushing portion 62, a pivot hole 66 aligned with the pivot hole 54 in the knee seat 5, and a first aperture 610 and a threaded slot 611 that are proximate to the free end 625 of the upper pushing portion 62 and that are in spatial communication with the slit 60. Each of the shaft holes 63, 64 has a top part partially communicated with the slit 60.

The upper pushing portion 62 is formed with a second aperture 620 having an upper receiving section 621 in spatial communication with the receiving groove 511, and a lower threaded section 622 in spatial communication with the first aperture 610 and the slit 60 and spaced apart from the first aperture 610 at a predetermined distance. The upper pushing portion 62 is further formed with a receiving slot 623 in spatial communication with the threaded slot 611 and the slit 60. The receiving slot 623 and the threaded slot 611 are located adjacent to the free end 625 of the upper pushing portion 62 of the movable member 6. The first and second apertures 610, 620 are located adjacent to and behind the receiving and threaded slots 623, 611 and distal to the free end 625.

The movable member 6 further includes two shafts 65, 65' disposed respectively within the shaft holes 63, 64, and two C-shaped elastic sleeves 650 disposed respectively within the shaft holes 63, 64, sleeved respectively on the shafts 65, 65' and abutting against the upper pushing portion 62.

A linkage 67 is adapted to be connected to the prosthetic lower leg of the prosthesis wearer, and has front and rear link units 671, 672 connected fixedly and respectively to the shafts 65, 65'.

The upper pushing portion 62 of the movable member 6 is movable toward the lower mounting portion 61 so as to cooperate with the same to clamp the shafts 65, 65' within the sleeves 650, respectively, to thereby prevent relative movement of the front and rear link units 671, 672, and is movable away from the lower mounting portion 61 so as to allow for relative movement of the front and rear links 671, 672.

The weight-buffering device 7 includes a rubber cushion 70, a metal plate 70', a control member 71, and a lock bolt 72. The rubber cushion 70 is disposed between the top portion 50 of the knee seat 5 and the upper pushing portion 62 of the movable member 6, and is disposed directly under the slant screw hole 56. The metal plate 70' is attached fixedly to a top surface of the rubber cushion 70. The control member 71, in this embodiment, is configured as an externally threaded rod engaged to the slant screw hole 56 and having a bottom end abutting against the metal plate 70'. The lock bolt 72 engages the threaded hole 57, and abuts against one side of the control member 71 for locking the control member 71 releasably within the slant screw hole 56.

The buffer adjustment device 8 includes a buffer cushion 80 and an adjustment bolt 81. The buffer cushion 80 is disposed within the upper receiving section 621 of the second aperture 620, protrudes partially out of the upper pushing portion 62 of the movable member 6, and is spaced apart from the projection 58. The adjustment bolt 81 has a lower section extending into the first aperture 610, and an upper section engaging the lower threaded section 622 of the second aperture 620. A top end of the adjustment bolt 81 abuts against a bottom end of the buffer cushion 80.

The restoring device 9 includes an elastic body 90 and a screw 91. The elastic body 90 is disposed in the receiving slot 623 of the upper pushing portion 62 of the movable member 6. The screw 91 engages the threaded slot 611 in the lower mounting portion 61 of the movable member 6, and has a top end abutting against a bottom end of the elastic body 90. Therefore, the screw 91 is operable by a tool, such as a screwdriver (not shown), so as to move the free end 625 of the upper pushing portion 62 relative to the lower mounting portion 61.

During normal walking of a prosthesis wearer, the weight-buffering device 7 is adjusted so as to match the weight of the prosthesis wearer that acts to apply a pressing force against the knee seat 5 of the prosthetic knee joint of the present invention. Hence, a buffering force can be increased or decreased as needed so that during normal walking by the prosthesis wearer, a large downward movement of the knee seat 5 can be prevented.

Figure 3:
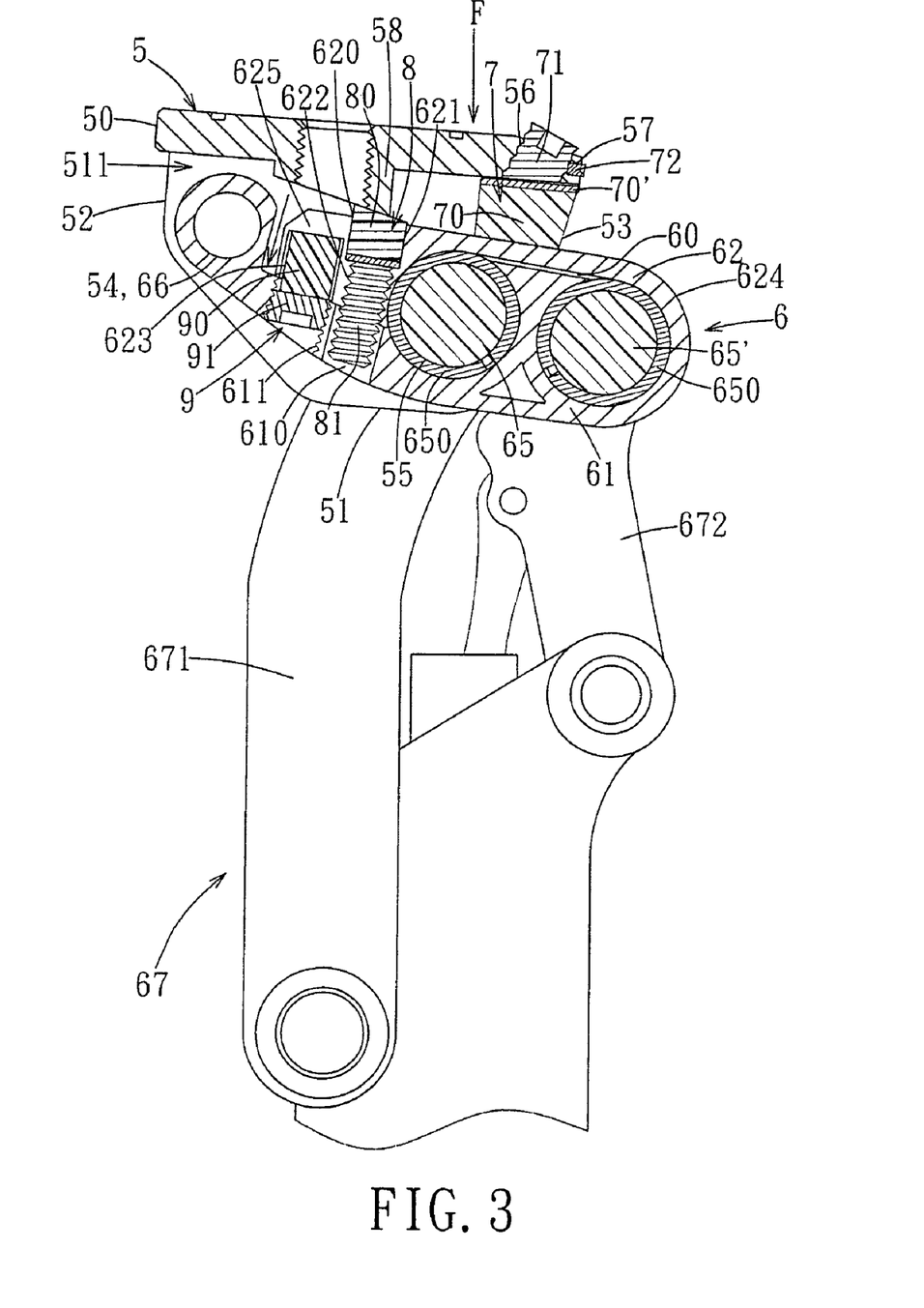
FIG. 3 is a view similar to FIG. 2, but with the prosthetic knee joint in a braking state.

When walking down a sloped surface, a normal body reaction is to lean rearward to adjust the center of gravity so that falling forwardly is prevented. Referring to FIG. 3, when the prosthesis wearer performs such shifting of weight, a large force (F) presses suddenly on the weight-buffering device 7 so that the weight-buffering device 7 is deformed, and the projection 58 of the knee seat 5 is pressed against the buffer cushion 80 so as to generate an initial mild buffering force. When this buffering force is not enough to counteract the large force (F), the free end 625 of the upper pushing portion

62 of the movable member 6 moves downwardly relative to the lower mounting portion 61 so as to press against the elastic body 90 of the restoring device 9 to store an energy. Simultaneously, the slit 60 gradually becomes smaller as the upper pushing portion 62 presses toward the lower mounting portion 61 and cooperates with the same to clamp the sleeves 650 therebetween, thereby stopping rotation of the shafts 65, 65'. Hence, the movement of the linkage 67 is also stopped at this time. This braking action prevents the prosthesis wearer from falling.

Figure 5:
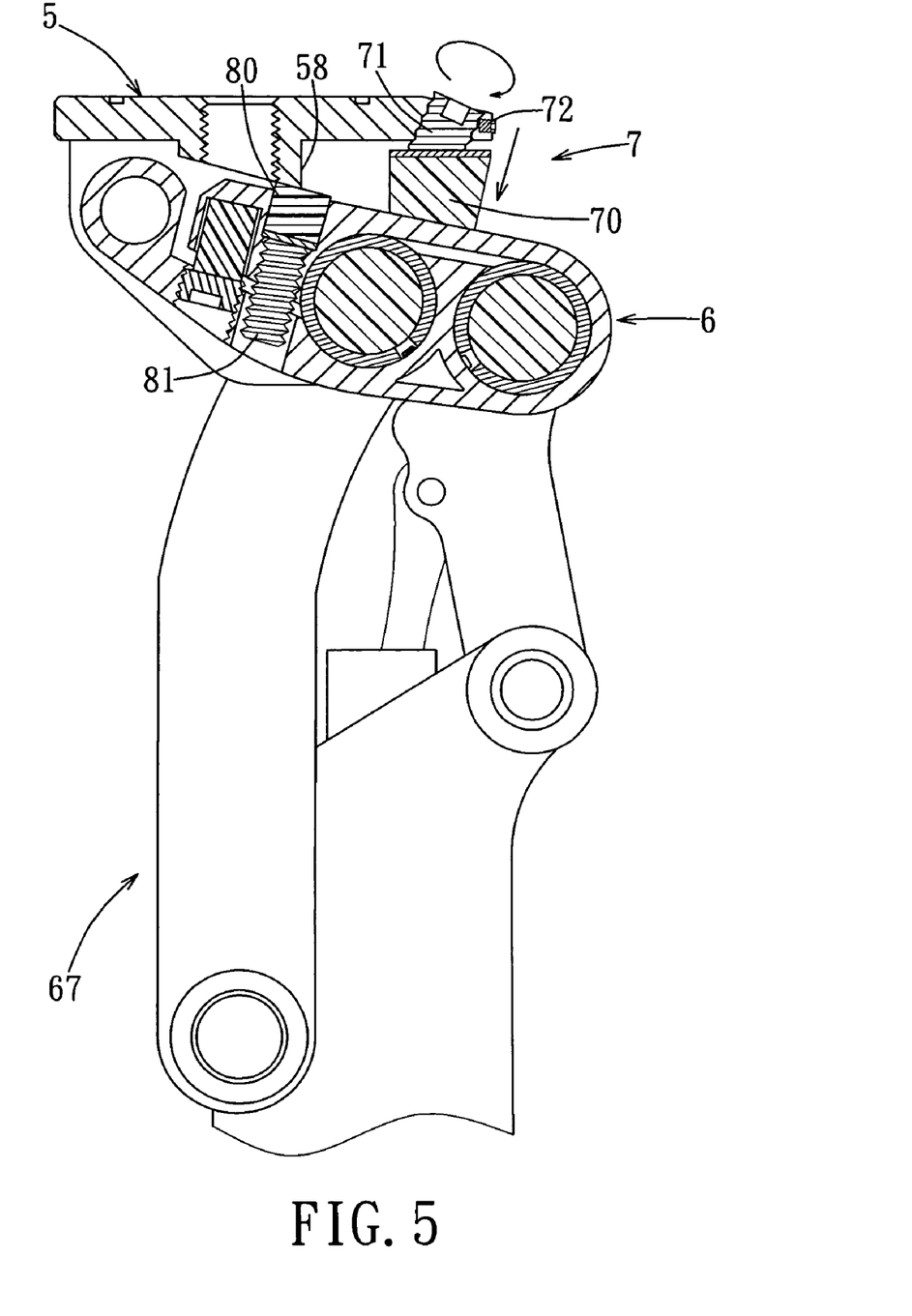
FIG. 5 illustrates how the prosthetic knee joint of the present invention is adjusted to suit the weight of a prosthetic wearer.

With reference to FIG. 5, when the prosthesis wearer has a low body weight, the lock bolt 72 is loosened to permit operation of the control member 71. When the control member 71 is turned to be displaced downwardly, a pressing force of the control member 71 on the rubber cushion 70 of the weight-buffering device 7 is increased, and an upward buffering force of the rubber cushion 70 is reduced. Hence, such adjustment on the weight-buffering device 7 results in earlier triggering of the braking action, which is suitable for a prosthesis wearer with a low body weight. When the control member 71 is turned to be displaced upwardly, the pressing force of the control member 71 on the rubber cushion 70 is reduced, and the upward buffering force of the rubber cushion 70 is increased. Such adjustment results in delayed triggering of the braking action, which is suitable for a prosthesis wearer having a larger body weight. The weight-buffering device 7 can thus be adjusted so as to vary the triggering of the braking operation of the movable member 6.

Figure 6:
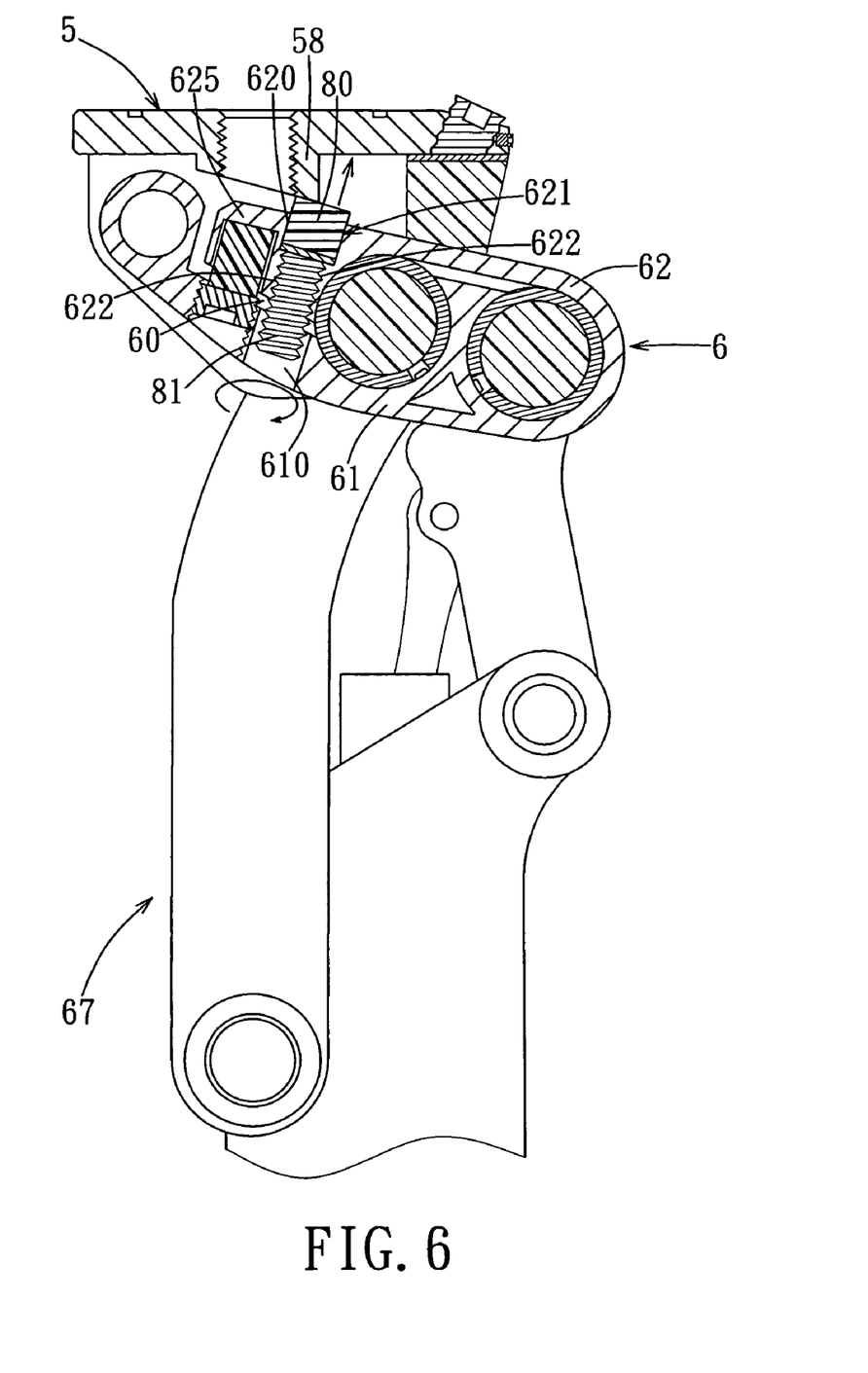
FIG. 6 illustrates how the prosthetic knee joint of the present invention is adjusted to delay a braking action.

With particular reference to FIG. 6, a screwdriver (not shown) may be inserted into the first aperture 610 so as to turn the adjustment bolt 81 to be displaced upwardly, thereby moving the buffer cushion 80 upwardly to abut against the projection 58. As such, when the large force (F) is sufficient to overcome the buffering force of the weight-buffering device 7, the projection 58 can be immediately pressed against the buffer cushion 80 so that the free end 625 of the upper pushing portion 62 of the movable member 6 can more quickly move downwardly to trigger the braking action. When the adjustment bolt 81 is turned to be displaced downwardly, with particular reference to FIG. 5, the buffer cushion 80 is lowered. As such, when the large force (F) is sufficient to overcome the buffering force of the weight-buffering device 7, the projection 58 presses against the buffer cushion 80 in a delayed manner, thereby delaying the triggering of the braking action.

Figure 7:
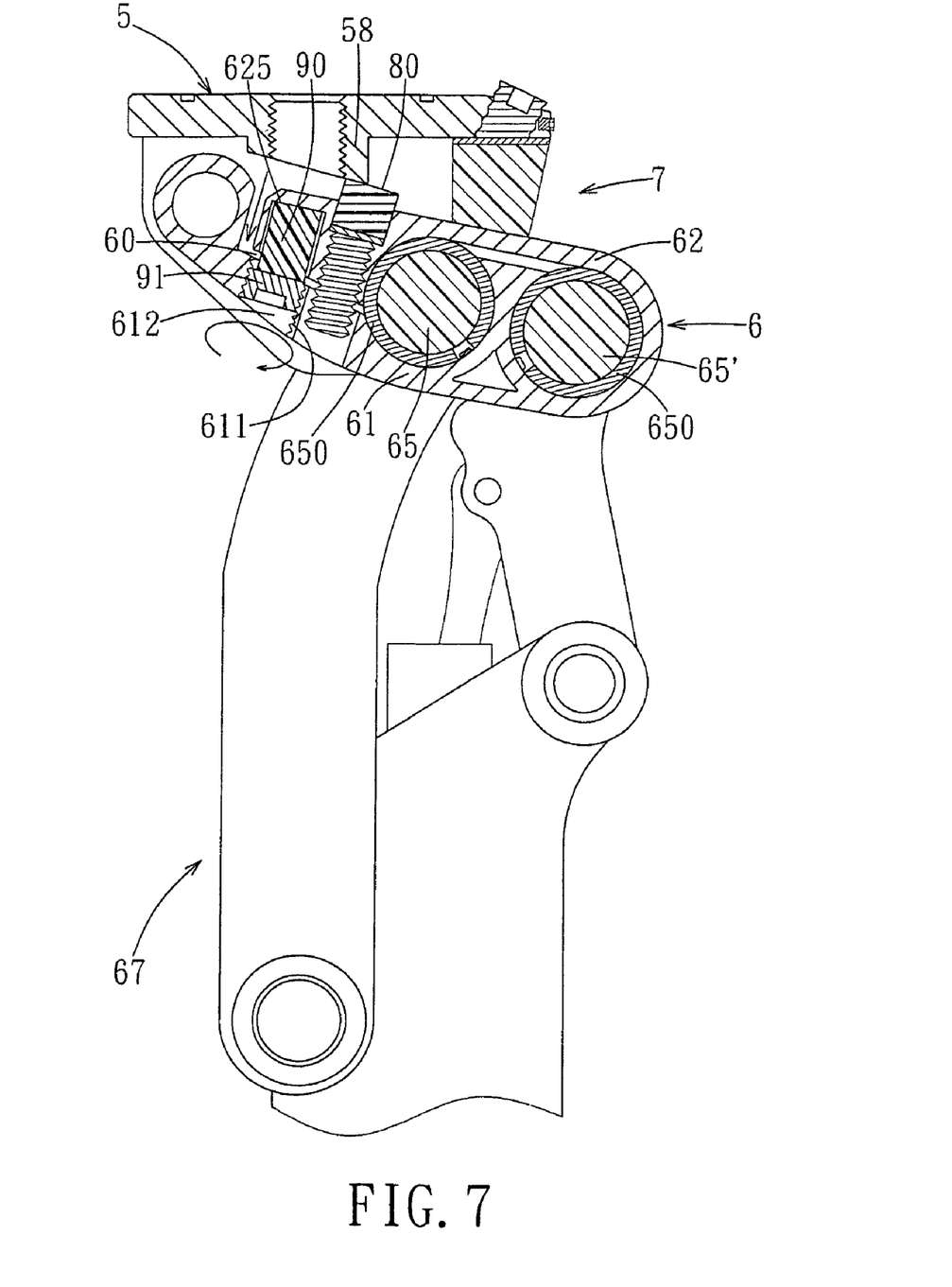
FIG. 7 illustrates another way of adjusting the prosthetic knee joint of the present invention to delay a braking action.

With reference to FIG. 7, when the screwdriver is inserted into the threaded slot 611 so as to turn the screw 91 to be displaced downwardly, the free end 625 of the upper pushing portion 62 of the movable member 6 moves downwardly, and the slit 60 gradually becomes smaller. Hence, with just a slight downward force applied to the upper pushing portion 62, the slit 60 can be reduced significantly such that the shafts 65, 65' are clamped respectively within the sleeves 650 so as to stop rotation of the shafts 65, 65'. As a result, the braking action can be more immediately executed. When the screw 91 is turned to be displaced upwardly so as to push the elastic body 90 upwardly, the slit 60 becomes larger, and a larger downward force is needed to lock the shafts 65, 65' within the sleeves 650, respectively, thereby delaying the braking action.

Figure 8:
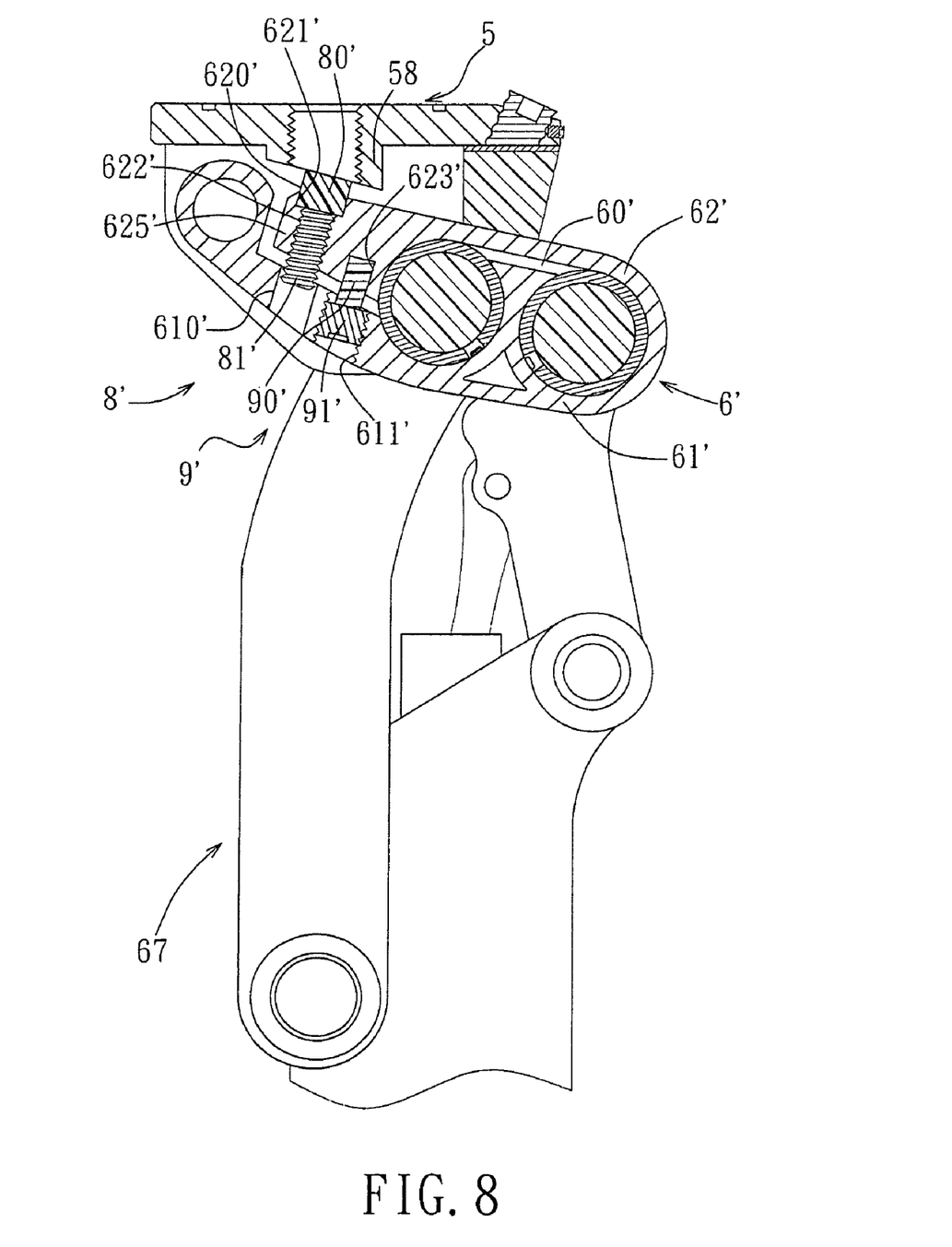
FIG. 8 is a partly sectional view of the second preferred embodiment of a prosthetic knee joint according to the present invention.
Figure 9:
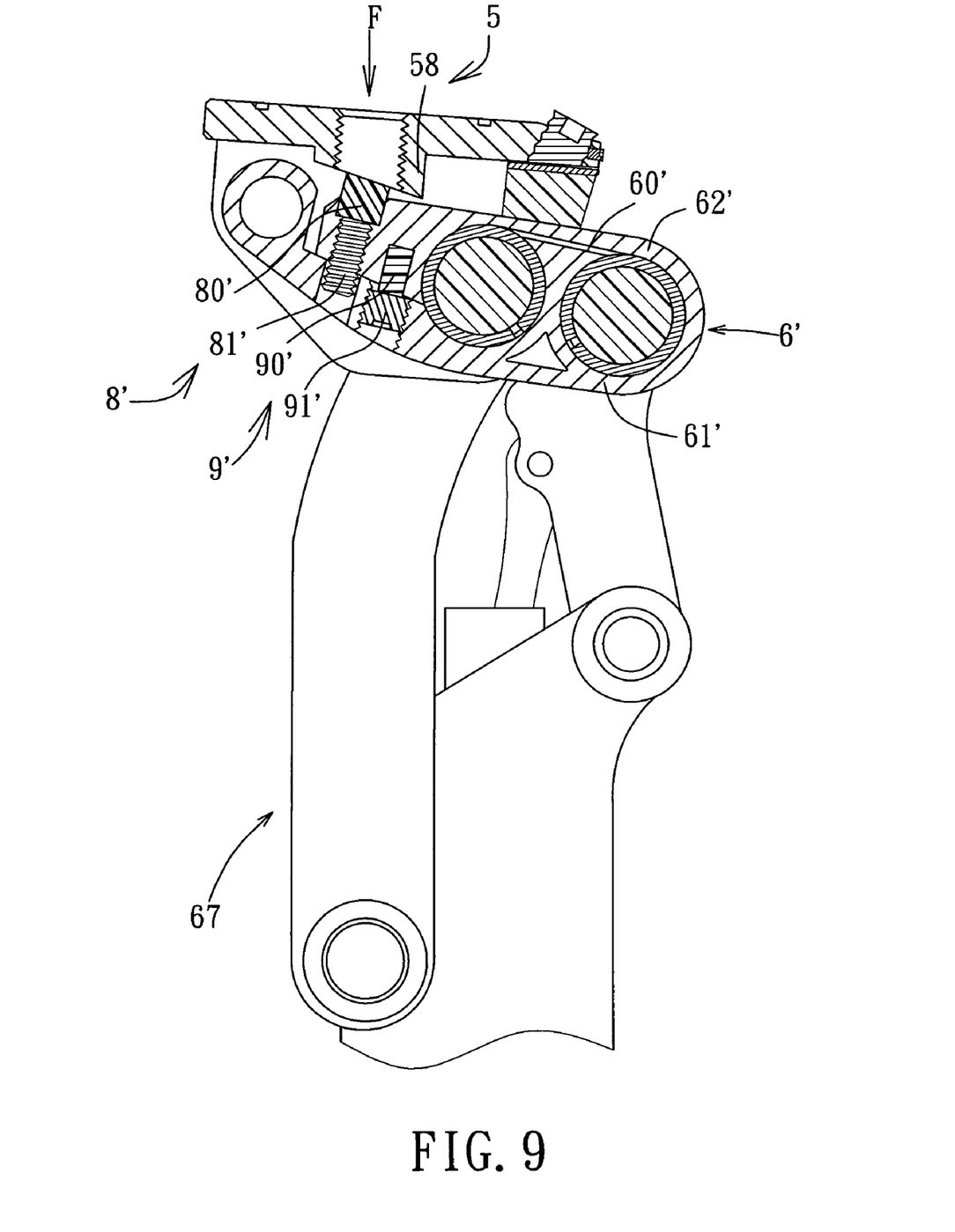
FIG. 9 is a view similar to FIG. 8, but with the prosthetic knee joint in a braking state.

FIGS. 8 and 9 illustrate the second preferred embodiment of a prosthetic knee joint according to the present invention. Unlike the first preferred embodiment, the first and second apertures 610', 620' are located adjacent to the free end 625' of the upper pushing portion 62' of the movable member 6', and the receiving and threaded slots 623', 611' are located adjacent to and behind the first and second apertures 610', 620'.

The buffer cushion 80' of the buffer adjustment device 8' is similarly disposed in the upper receiving section 621' of the second aperture 620', and protrudes partially out of the upper pushing portion 62' of the movable member 6' so as to abut against the projection 58 of the knee seat 5. The adjustment bolt 81' is engaged to the lower threaded section 622' of the second aperture 620', and the top end thereof abuts against the bottom end of the buffer cushion 80'. The elastic body 90' of the restoring device 9' is disposed in the receiving slot 623' of the upper pushing portion 62'. The screw 91' is engaged to the threaded slot 611', and the top end thereof abuts against the bottom end of the elastic body 90'. The changes in position between the buffer adjustment device 8' and the restoring device 9' do not affect the braking action of the prosthetic knee joint of the present invention when the prosthesis wearer walks down the sloped surface. Since the braking action shown in FIG. 9 is similar to that shown in FIG. 3, a detailed description of the same is dispensed herewith for the sake of brevity.

While the present invention has been described in connection with what are considered the most practical and preferred embodiments, it is understood that this invention is not limited to the disclosed embodiments but is intended to cover various arrangements included within the spirit and scope of the broadest interpretation so as to encompass all such modifications and equivalent arrangements.

I claim:

1. A prosthetic knee joint adapted to be connected between a prosthetic thigh and a prosthetic lower leg, said prosthetic knee joint comprising:

a knee seat having a top portion adapted to be connected with the prosthetic thigh, a bottom portion connected fixedly to said top portion and defining a receiving groove, a projection projecting downwardly from said top portion into said receiving groove, a slant screw hole formed in a rear end of said top portion, and a threaded hole transverse to and in spatial communication with said slant screw hole;

a movable member disposed pivotally in said receiving groove, and including a lower mounting portion connected pivotally to said bottom portion of said knee seat, an upper pushing portion having a connecting end connected integrally to said lower mounting portion and a front free end movable upwardly and downwardly relative to said lower mounting portion, and a slit defined between said lower mounting portion and said upper pushing portion, said lower mounting portion being formed with two spaced-apart shaft holes extending in a left-to-right direction and proximate to said connecting end of said upper pushing portion, and a first aperture and a threaded slot that are proximate to said free end of said upper pushing portion and that are in spatial communication with said slit, each of said shaft holes having a top part partially communicated with said slit, said upper pushing portion being formed with a second aperture having an upper receiving section in spatial communication with said receiving groove, and a lower threaded section in spatial communication with said first aperture and said slit and spaced apart from said first aperture at a predetermined distance, said upper pushing portion being further formed with a receiving slot in spatial communication with said threaded slot and said slit, said movable member further including two shafts disposed respectively within said shaft holes, and two C-shaped elastic sleeves disposed respectively within said shaft holes, sleeved respectively on said shafts, and abutting against said upper pushing portion;

a linkage adapted to be connected to the prosthetic lower leg, and having front and rear link units connected fixedly and respectively to said shafts, said upper pushing portion being movable toward said lower mounting portion so as to cooperate with said lower mounting portion to clamp said shafts within said sleeves, respectively, to thereby prevent relative movement of said front and rear link units, and being movable away from said lower mounting portion so as to allow for relative movement of said front and rear link units;

a weight-buffering device including a rubber cushion disposed between said top portion of said knee seat and said upper pushing portion of said movable member and disposed directly under said slant screw hole, an externally threaded control member engaging said slant screw hole and having a bottom end abutting against said rubber cushion, and a lock bolt engaging said threaded hole and abutting against said control member for locking said control member releasably within said slant screw hole;

a buffer adjustment device including a buffer cushion disposed within said upper receiving section of said second aperture and protruding partially out of said movable member so as to abut against said projection, and an adjustment bolt having a lower section extending into said first aperture, and an upper section engaging said lower threaded section of said second aperture and abutting against a bottom end of said buffer cushion, said adjustment bolt being adjustable so as to allow said buffer cushion to move away from said projection; and a restoring device including an elastic body disposed in said receiving slot, and a screw engaging said threaded slot and having a top end abutting against a bottom end of said elastic body, said screw being operable so as to move said free end of said upper pushing portion relative to said lower mounting portion.

2. The prosthetic knee joint of claim 1, wherein said receiving slot and said threaded slot are located adjacent to said free end of said upper pushing portion of said movable member, said first and second apertures being located adjacent to and behind said receiving and threaded slots and distal to said free end.

3. The prosthetic knee joint of claim 1, wherein said first and second apertures are located adjacent to said free end of said upper pushing portion of said movable member, said receiving and threaded slots being located adjacent to and behind said first and second apertures.

* * * * *